United States Patent

Yamada et al.

[11] 3,974,031
[45] Aug. 10, 1976

[54] PROCESS FOR PRODUCING L-CYSTEINE OR ITS DERIVATIVES

[75] Inventors: Hideaki Yamada; Hidehiko Kumagai, both of Kyoto; Haruyiki Ohkishi, Sagamihara, all of Japan

[73] Assignee: Mitsubishi Chemical Industries Ltd., Tokyo, Japan

[22] Filed: May 6, 1975

[21] Appl. No.: 575,009

[30] Foreign Application Priority Data
May 9, 1974 Japan.................................. 49-51496
May 10, 1974 Japan................................ 49-51926

[52] U.S. Cl.................................. 195/29; 195/30; 195/47
[51] Int. Cl.² ........................................ C12D 13/06
[58] Field of Search........................... 195/29, 30, 47

[56] References Cited
OTHER PUBLICATIONS
Proceedings of the Joint U.S.-U.S.S.R. Symposium on Biological Pyridoxal Catalysis; Leningrad, U.S.S.R. (Aug. 16-23, 1974) p. 155.

*Primary Examiner*—A. Louis Monacell
*Assistant Examiner*—Robert J. Warden
*Attorney, Agent, or Firm*—Oblon, Fisher, Spivak, McClelland & Maier

[57] ABSTRACT
L-cysteine and derivatives thereof of the formula (I):

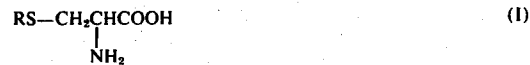

wherein R is selected from the group consisting of hydrogen, $C_1$-$C_{15}$ alkyl, $C_2$-$C_{15}$ alkenyl, $C_6$-$C_{15}$ aryl, $C_7$-$C_{15}$ aralkyl, are prepared by a process which comprises reacting β-substituted L-alanine having the formula (II):

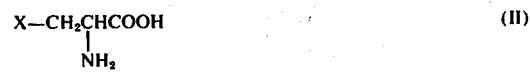

wherein X is selected from the group consisting of halogen, —OR' and —SR'; wherein R' is selected from the group consisting of hydrogen, allyl, $C_1$-$C_{15}$ alkyl, $C_6$-$C_{15}$ aryl and $C_7$-$C_{15}$ aralkyl, with a thiol, or hydrogen sulfide, of the formula (III):

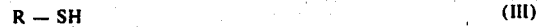

wherein R is as defined above, ammonium hydrosulfide of a metal hydrosulfide of the formula (IV):

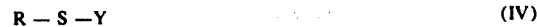

wherein R is hydrogen, and Y is ammonium or a metal, in an aqueous medium, in the presence of cysteine desulfhydrase.

22 Claims, No Drawings

PROCESS FOR PRODUCING L-CYSTEINE OR ITS DERIVATIVES

BACKGROUND OF THE INVENTION

1. Field of the Invention

The present invention relates to a process for producing L-cysteine or a derivative thereof in the presence of cysteine desulfhydrase which is derived mainly from microorganisms.

2. Description of the Prior Art

L-Cysteine is a quasi-essential amino acid which is useful as a food additive and a pharmaceutical, e.g., as an antidote. In addition, L-cysteine is useful as an intermediate in the preparation of other pharmaceutical compounds. The derivatives of L-cysteine, for example, the sulfoxides of S-methyl-L-cysteine and S-allyl-L-cysteine, are known to suppress increasing levels of cholesterol in blood and liver.

The known processes for the production of cysteine include: (1) extraction of cystine from a hydrolysate of natural products such as man's hair, followed by reduction of cystine; (2) condensation of benzyl chloromethyl sulfide with diethyl phthalimidomalonate, followed by hydrolysis and reduction; (3) hydrolysis of the thiazoline derivative obtained by the reaction of N-thiobenzoylserine with thionyl chloride; and (4) enzymatic processes. Among these processes, organic synthesis are unfavorable because of high production costs due to the complicated nature of the reactions and the racemic resolutions required to obtain L-cysteine.

The known enzymatic processes include: (1) synthesis of L-cysteine from serine and hydrogen sulfide in the presence of cysteine synthetase derived from *Neurospora crassa* (OLS 2,225,797; J. Biol. Chem., 242, 12 (1967)); (2) synthesis of L-cysteine from serine and hydrogen sulfide in the presence of serine sulfhydrase (Biochemische Zeitschrift 336, 258–273 (1962)); (3) synthesis of L-cysteine from β-chloroalanine and hydrogen sulfide in the presence of serine sulfhydrase. (Proceedings of the Joint U.S.-U.S.S.R. Symposium on Biological Pyridoxal Catalysis; Leningrad, U.S.S.R. (August 16–23, 1974) P.155); and (4) synthesis of L-cysteine from methionine and serine in the presence of dandruff of animals. (Japanese Pat. published No. 16019/1962, Chemical Abstracts 57 5150i). These enzymatic processes, however, are not always suitable for industrial production of L-cysteine. Consequently, it would be most desirable to have a new enzymatic process free of this defect.

SUMMARY OF THE INVENTION

Accordingly, it is an object of this invention to produce L-cysteine and derivatives thereof economically and in high yields by an enzymatic process suitable for industrial use.

This and other objects of this invention, as will hereinafter be made clear from the ensuing discussion, have been attained by providing a process wherein L-cysteine is obtained in high yields from the reaction of β-substituted L-alanine and a compound selected from the group consisting of hydrogen sulfide, ammonium hydrosulfide, a metal hydrosulfide, ammonium sulfide and a metal sulfide which is capable of producing such a metal hydrosulfide and/or hydrogen sulfide in an aqueous medium, in the presence of the above enzyme. Derivatives of L-cysteine are obtained in high yields from the reaction of β-substituted L-alanine and a thiol in the presence of the above enzyme.

DESCRIPTION OF THE PREFERRED EMBODIMENTS

The method of the present invention is illustrated by the following reaction sequence scheme:

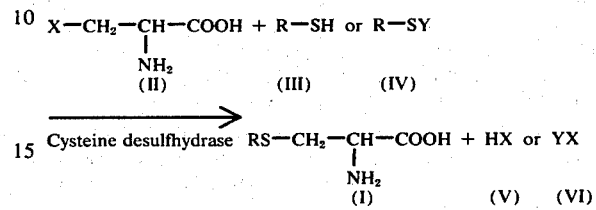

wherein R is selected from the group consisting of hydrogen, $C_1 - C_{15}$ alkyl, $C_2 - C_{15}$ alkenyl, $C_6 - C_{15}$ aryl and $C_7 - C_{15}$ aralkyl; X is selected from the group consisting of halogen, —OR' and —SR' wherein R' is selected from the group consisting of hydrogen, allyl, $C_1 - C_{15}$ alkyl, $C_6 - C_{15}$ aryl and $C_7 - C_{15}$ aralkyl; and R — SY is ammonium hydrosulfide or a metal hydrosulfide wherein R is hydrogen and Y is ammonium or a metal such as an alkali or alkaline earth metal. This reaction is a replacement reaction whereby the leaving group X of formula (II) is replaced by the group RS of formula (III) or (IV) to form L-cysteine or a derivative thereof of the formula (I).

β-substituted L-alanines (II) suitable as the starting material for the present invention include: β-halogeno-L-alanines, such as β-chloro-L-alanine, β-bromo-L-alanine and β-iodo-L-alanine; O-alkyl-L-serines, such as O-methyl-L-serine, O-ethyl-L-serine and O-(n-hexyl)-L-serine; O-aryl-L- serines, such as O-phenyl-L-serine; O-aralkyl-L-serines, such as O-benzyl-L-serine; S-alkyl-L-cysteines, such as S-methyl-L-cysteine, S-ethyl-L-cysteine and S-(n-hexyl)-L-cysteine; S-aryl-L-cysteines, such as S-phenyl-L-cysteine; S-aralkyl-L-cysteines, such as S-benzyl-L-cysteine; L-serine; L-cysteine; S-allyl-L-cysteine and O-allyl-L-serine. The preferred β-substituted alanines are β-chloro-L-alanine, L-serine and L-cysteine.

It is preferred that the metal hydrosulfide employed as the other starting material be soluble in water. Suitable such metal hydrosulfides include a hydrosulfide of an alkali metal such as sodium hydrosulfide, potassium hydrosulfide, lithium hydrosulfide, and a hydrosulfide of an alkaline earth metal such as calcium hydrosulfide, magnesium hydrosulfide, barium hydrosulfide and strontium hydrosulfide. In place of the metal hydrosulfide, there may be employed a metal sulfide which is capable of producing a water-soluble metal hydrosulfide and/or hydrogen sulfide in an aqueous medium. Suitable such metal sulfides include sulfides of an alkali metal, such as sodium sulfide, potassium sulfide, and lithium sulfide, and sulfides of an alkaline earth metal, such as calcium sulfide, magnesium sulfide, barium sulfide and strontium sulfide. Likewise, instead of ammonium hydrosulfide, ammonium sulfide may be employed since it produces ammonium hydrosulfide and/or hydrogen sulfide in an aqueous medium. Suitable thiols for use as the starting material for the production of derivatives of L-cysteine include: alkanethiols, such as methanethiol, ethanethiol, n-propanethiol, n-octanethiol and the like; alkenethiols, such as 2-propenethiol, 3-pentenethiol, 3-octenethiol and the like; aryl mercaptans, such as thiophenol, naphthalenethiol and the like; and aralkyl mercaptans, such as phenylmethanethiol, 2-phenylethanethiol and the like.

The cysteine desulfhydrase employed in the present invention is an enzyme which is known as a catalyst for the reaction wherein L-cysteine decomposes into pyruvic acid, ammonia and hydrogen sulfide (Biochem. Biophys. Res. Commun. 59 789 (1974)). This enzyme is readily produced by a variety of microorganisms. Such microorganisms which produce said enzyme include, for example, the microorganisms belonging to the following species: Brevibacterium, Sarcina, Corynebacterium, Arthrobacter, Pseudomonas, Proteus, Micrococcus, Escherichia, Serratia, Alcaligenes, Bacillus, Agrobacterium, Enterobacter (Aerobacter), Citrobacter, Klebsiella and Salmonella. But the microorganisms suitable for producing the enzyme are not limited to the aforementioned types. Any microorganism which produces the above enzyme may be employed. Suitable examples of such microorganisms include: *Sarcina lutea* (IAM 1099), *Corynebacterium equi* (IAM 1038), *Arthrobacter simplex* (IFO 3530), *Brevibacterium ammoniagenes* (IFO 12071), *Pseudomonas fluorescens* (IFO 3081), *Proteus morganii* (IFO 3848), *Micrococcus roseus* (IFO 3764), *Citrobacter freundii* (IFO 12681), *Escherichia coli* (IFO 3301), *Serratia marcescens* (IFO 3054). *Agrobacterium tumefaciens* (IAM 1037), *Alcaligenes faecalis* (IAM 1015), *Bacillus subtilis* (IFO 3009), *Enterobacter aerogenes* (*Aerobacter aerogenes*) (IFO 3320), *Enterobacter cloacae* (IFO 12009), *Klebsiella pneumoniae* (IFO 3512), *Salmonella typhimurium* (IFO 12529) and the like.

A suitable method employing these microorganisms for production of cysteine desulfhydrase used in the present invention is summarized as follows. The nutrients necessary for the incubation of these microorganisms are a carbon source, a nitrogen source and an inorganic salt source. Suitable carbon sources include glucose, sucrose, fructose, mannose, mannitol, xylose, glycerol, sorbitol, molasses, starch hydrolysate and the like; organic acids such as acetic acid, fumaric acid and the like; and n-paraffin and the like. Suitable nitrogen sources include ammonia; ammonium salts of organic acids and inorganic acids such as ammonium chloride, ammonium sulfate, ammonium carbonate, ammonium acetate and the like; nitrates such as sodium nitrate, potassium nitrate, ammonium nitrate and the like; corn steep liquor, yeast extract, meat extract, yeast powder, cotton seed powder, soybean powder, soybean hydrolysate, peptone, polypeptone and the like. Suitable inorganic salts include potassium phosphate, sodium phosphate, magnesium sulfate and the like.

The incubation temperature can range from 20° to 80°C, preferably from 25° to 50°C. The aerobic incubation is carried out for a period of 10 to 72 hours. It is preferred to maintain the pH of the medium in the range of 7 to 11 during the incubation. The presence of 0.1 – 1 weight percent of at least one amino acid selected from the group consisting of L-cysteine, L-cystine, S-methyl-L-cysteine, S-ethyl-L-cystiene L-serine and O-methyl-L-serine further enhances the yield of said enzyme. The cysteine desulfhydrase obtained by the above process is mainly present intracellularly. The usual methods such as ultrasonic treatment, fractionation with ammonium sulfate an ion exchange chromatography are applicable to the separation and purification of cysteine desulfhydrase. The molecular weight of the obtained enzyme is 150,000 – 500,000. Pyridoxal phosphate is usually obtained as a coenzyme.

According to the present invention, β-substituted L-alanine reacts with a thiol or a compound selected from the group consisting of hydrogen sulfide, ammonium hydrosulfide, a metal hydrosulfide, ammonium sulfide and a metal sulfide which is capable of producing such a metal hydrosulfide and/or hydrogen sulfide in the aqueous medium employed, using a pH normally in the range of 6 to 12, more preferably in the range of 7 to 11, in the presence of the cysteine desulfhydrase derived mainly from microorganisms as described above. It is not required that the enzyme to be used be purified and crystallized. Any microorganism broth of living cells, dried cells, ground cells and cellular extracts which possesses the enzyme may be used. The amount of the enzyme to be used, defined as the weight of dried cells, is normally about 0.1 – 20 g/l, more preferably 1 – 5 g/l. The reaction temperature ranges generally from 20° to 80°C, more preferably from 30° to 50°C. The reaction period varies from 1 to 100 hours dependent upon the activity of the enzyme, the concentration and the species of the substrate, and the reaction temperature. The time of reaction will normally be between 2 hours and 48 hours. The concentrations of the β-substituted L-alanine and the thiol or the compound selected from the group consisting of hydrogen sulfide, ammonium hydrosulfide, a metal hydrosulfide, ammonium sulfide and a metal sulfide are normally each 1 – 40 weight percent, more preferably 3 – 20 weight percent.

The addition of a carbonyl compound containing 1 to 20 carbon atoms to said aqueous reaction medium results in an increase in the yield of L-cysteine or derivative thereof. Representative of such compounds are α-keto carboxylic acids containing 3 to 20 carbon atoms, such as pyruvic acid, 2-oxobutyric acid, 2-oxoglutaric acid and the like; aldehydes containing 1 to 20 carbon atoms, such as acetaldehyde, propionaldehyde, isobutyraldehyde, benzaldehyde and the like; and ketones containing 3 to 20 carbon atoms, such as acetone, methyl ethyl ketone, diethyl ketone, methyl isobutyl ketone, cyclohexanone, benzophenone, acetophenone, benzil and the like. The carbonyl compound can be added such that the concentration is from about 0.01 to 20 M to effect an increase in yields, with from about 0.05 to 10 M being preferred.

The presence of a small amount of pyridoxal phosphate in the reaction medium enhances the activity of the enzyme. Although the cells of the microorganisms from which the enzyme is derived contain a small amount of pyridoxal phosphate, further addition of this compound increases the activity of the enzyme. Pyridoxal phosphate should be added such that its concentration is up to 0.01 mM. The addition of pyridoxal phosphate to a concentration over 0.01 mM has no effect on the yield of L-cysteine or derivative thereof.

Upon completion of the reaction, L-cysteine or derivative thereof can be separated employing the usual procedures, for example, treatment with an ion exchange resin.

As has been previously described in detail, the present invention is an enzymatic process employing cysteine desulfhydrase as a catalyst making possible the stereospecific production of L-cysteine or its derivatives in high yields under mild reaction conditions from cheap starting materials.

Having generally described the invention, a more complete understanding can be obtained by reference to certain specific examples, which are included for purposes of illustration only and are not intended to be limiting unless otherwise specified. In the following examples, the identification and determination of the yields of L-cysteine and its derivatives were established using an amino acid analyser.

Reference Example 1

To a 500 ml. shaker flask was added 100 ml. of a nutrient medium with a pH of 7.5 having the following composition:

| | |
|---|---|
| L-cysteine.HCl | 0.1% |
| Yeast extract | 0.5% |
| Meat extract | 0.5% |
| Polypeptone | 0.5% |
| NaCl | 0.2% |

After the flask and its content were sterilized, the flask was inoculated with a section from the surface of an agar slant on which a variety of micro-organisms shown in Table 1 had been growing. The inoculated flask was incubated at 30°C for a period of 16 hours and the cells were collected by centrifugation. The cells obtained were washed with physiological saline, suspended in 100 ml. of phosphate buffer solution and destroyed by ultrasonic treatment. Then a cell extract liquid showing activity of the cysteine desulfhydrase was obtained by centrifugation. The results are shown in Table 1. The activity in Table 1 was determined by adding 1 ml. of said extract liquid into 4 ml. of the solution containing 2.0 ml. of $1 \times 10^{-1}$ M Tris-HCl buffer solution (pH 9), 0.4 ml. of $1 \times 10^{-3}$ M pyridoxal phosphate and 1.0 ml. of $1 \times 10^{-2}$ M L-cysteine, decomposing L-cysteine at 30°C for a period of 20 minutes and then determining the amount of pyruvic acid formed according to the method of Friedmann, T.E. and Haugen, G.E. (J. Biol. Chem. 147 415 (1943)). The activity of the enzyme is shown in u units, expressing the activity of the enzyme in terms of the base activity wherein 1 $\mu$-mole of L-cysteine is decomposed in a period of 1 minute (1 u unit).

Table 1

| Employed microorganism | | Activity of the enzyme ($\mu$) |
|---|---|---|
| Sarcina lutea | (IAM 1099) | 3.04 |
| Sarcina lutea | (IFO 3232) | 3.92 |
| Corynebacterium equi | (IAM 1038) | 0.16 |
| Arthrobacter simplex | (IFO 3530) | 0.04 |
| Brevibacterium ammoniagenes | (IFO 12071) | 0.57 |
| Pseudomonas fluorescens | (IFO 3081) | 1.28 |
| Proteus morganii | (IFO 3848) | 1.25 |
| Micrococcus roseus | (IFO 3764) | 0.68 |
| Citrobacter freundii | (IFO 12681) | 18.59 |
| Escherichia coli | (IFO 3301) | 4.55 |
| Serratia marcescens | (IFO 3054) | 0.92 |
| Alcaligenes faecalis | (IAM 1015) | 4.27 |
| Bacillus subtilis | (IFO 3009) | 0.92 |
| Agrobacterium tumefaciens | (IAM 1037) | 3.86 |
| Enterobacter aerogenes (Aerobacter aerogenes) | (IFO 3320) | 5.59 |
| Klebsiella pneumoniae | (IFO 3512) | 3.18 |
| Salmonella typhimurium | (IFO 12529) | 3.28 |

Reference Example 2

Forty liters of the nutrient medium having the same composition as that of Reference Example 1 was inoculated with Sarcina lutea and incubated at 30°C for 15 hours. The cells obtained were suspended in 0.1 M phosphate buffer solution (pH 7.0) and a cellular extract was obtained by ultrasonic treatment followed by centrifugation. The extract was fractionated by ammonium sulfate. The fraction having activity of cysteine desulfhydrase was dialyzed and chromatographed over DEAE-Sephadex, and the enzyme was adsorbed. The column was washed with 0.1 M phosphate buffer solution (pH 7.0) and the enzyme was eluted with 0.3 M phosphate buffer solution (pH 7.0). To the elute containing the cysteine desulfhydrase was added ammonium sulfate to 50% saturation. The enzyme was concentrated and dialyzed. The dialyzed solution containing the enzyme was subjected to a gel-filtration employing Sephadex G-150 and Sephadex G-200, and the active fraction was collected through a fraction collector. This elute containing the cysteine desulfhydrase was again fractionated with ammonium sulfate (0 – 30% saturation), and the purified enzyme was obtained. The cysteine desulfhydrase obtained as described above showed behavior as a single protein in disk electrophoresis analysis and possessed an activity of about 25 u/mg.

EXAMPLE 1

To 10 ml. of $5 \times 10^{-2}$ M ammonium buffer solution (pH 9.5) containing 270 mg of $\beta$-chloro-DL-alanine, $\beta$-chloro-L-alanine, L-serine or S-methyl-L-cysteine, and 150 mg of sodium sulfide was added 3 units of the purified enzyme obtained from Citrobacter freundii (IFO 12681), and the reaction was carried out at 30°C for 1 hour. L-cysteine was obtained in the amounts shown in Table 2.

Table 2

| Substrate | Amount of L-cysteine obtained (mg) |
|---|---|
| $\beta$-chloro-DL-alanine | 76.5 |
| $\beta$-chloro-L-alanine | 99.0 |
| L-serine | 4.7 |
| S-methyl-L-cysteine | 7.2 |

EXAMPLE 2

To 10 ml. of $5 \times 10^{-2}$ M ammonium buffer solution (pH 9.5) containing 250 mg of $\beta$-chloro-L-alanine and 150 mg of sodium sulfide was added 2.5 units of the purified enzyme obtained from Enterobacter aerogenes (Aerobacter aerogenes) (IFO 3320), and the reaction was carried out at 30°C for 1 hour. 98 mg. of L-cysteine was obtained.

EXAMPLE 3

To a large test tube was added 10 ml. of a nutrient medium with a pH of 7.5 having the following composition:

| | |
|---|---|
| 0.2% | L-Cysteine |
| 0.5% | Yeast extract |
| 0.5% | Meat extract |
| 0.5% | Polypeptone |
| 0.2% | NaCl |

After the tube and its content were sterilized, the tube was inoculated with a section from the surface of an agar slant on which a variety of microorganisms shown in Table 3 had been growing. The inoculated tube was incubated at 30°C for a period of 16 hours and the cells were collected by centrifugation. The cells obtained were added to 2 ml. of 5 × 10⁻² M ammonium buffer solution (pH 9.5) containing 50 mg of β-chloro-L-alanine and 30 mg of sodium sulfide, and the reaction was carried out at 30°C for 1 hour. L-Cysteine was obtained in the reaction liquid in the amounts shown in Table 3.

Table 3

| Microorganism | | L-Cysteine (mg/ml) |
|---|---|---|
| Sarcina lutea | (IAM 1099) | 4.3 |
| Corynebacterium equi | (IAM 1038) | 4.5 |
| Arthrobacter simplex | (IFO 3530) | 1.2 |
| Brevibacterium ammoniagenes | (IFO 12071) | 2.8 |
| Pseudomonas fluorescens | (IFO 3081) | 2.9 |
| Proteus morganii | (IFO 3848) | 2.6 |
| Micrococcus roseus | (IFO 3764) | 1.4 |
| Citrobacter freundii | (IFO 12681) | 10.1 |
| Escherichia coli | (IFO 3301) | 7.7 |
| Serratia marcescens | (IFO 3054) | 1.6 |
| Alcaligenes faecalis | (IAM 1015) | 8.1 |
| Bacillus subtilis | (IFO 3009) | 1.3 |
| Agrobacterium tumefaciens | (IAM 1037) | 4.5 |
| Enterobacter aerogenes (Aerobacter aerogenes) | (IFO 3320) | 9.8 |
| Klebsiella pneumoniae | (IFO 3512) | 4.3 |
| Salmonella typhimurium | (IFO 12529) | 5.1 |

EXAMPLE 4

The organism *Enterobacter aerogenes* (*Aerobacter aerogenes*) (IFO 3320) was maintained on a medium with a pH of 7.5 containing the following ingredients:

| | |
|---|---|
| 0.2% | L-Cysteins |
| 0.5% | Yeast extract |
| 0.5% | Meat extract |
| 0.5% | Polypeptone |
| 0.1% | Glycerol |
| 0.2% | $CaCl_2$ |
| 0.2% | NaCl |

Adequate growth was obtained in 16 hours at 30°C. The cells were collected by centrifugation. The cells obtained from 10 ml of the medium (the activity of the enzyme: about 6 u) were added to 10 ml of 5 × 10⁻¹ M ammonium buffer solution (pH 9.5) containing 5 mmol. of β-chloro-L-alanine, 5 mmol. of a sulfide or a hydrosulfide shown in Table 4, 0.05% sodium dodecyl sulfate and pyridoxal phosphate in a concentration of 0.1 mM, and the reaction was carried out at 30°C for 3 hours. L-Cysteine was formed in the amounts shown in Table 4.

Table 4

| Sulfides or hydrogen sulfides | L-cysteine formed (mmole) |
|---|---|
| $Na_2S$ | 1.62 |
| NaSH | 1.06 |
| $(NH_4)_2S$ | 0.54 |
| CaS | 0.20 |
| BaS | 0.32 |
| $K_2S$ | 0.58 |
| KSH | 0.43 |

EXAMPLE 5

The cells obtained from 10 ml. of the medium in Example 4 were added to 10 ml. of 5 × 10⁻¹ M ammonium buffer solution containing 5 mmol. of β-chloro-L-alanine, 5 mmol. of sodium sulfide, 0.05% sodium dodecyl sulfate and an amount of pyridoxal phosphate to achieve the concentration shown in Table 5. The reaction was carried out at 30°C for 3 hours. L-Cysteine was formed in the amounts shown in Table 5.

Table 5

| Pyridoxal phosphate (mM) | L-cysteine formed (mmole) |
|---|---|
| 0 | 0.43 |
| 0.01 | 1.02 |
| 0.04 | 1.02 |
| 0.1 | 1.00 |
| 0.4 | 1.08 |
| 1 | 1.14 |
| 2 | 1.08 |

EXAMPLE 6

The organism *Enterobacter cloacae* (*Aerobacter cloacae*) (IFO 12009) was maintained on a medium with a pH of 7.2 containing the following ingredients:

| | |
|---|---|
| 0.2% | L-Cysteine |
| 1.0% | Glucose |
| 1.0% | Yeast powder |
| 4.0% | Soybean hydrolysate |
| 0.2% | $KH_2PO_4$ |
| 0.1% | $MgSO_4.7H_2O$ |
| 0.001% | $FeSO_4.7H_2O$ |
| 0.1% | $(NH_4)_2SO_4$ |

Adequate growth was obtained in 18 hours at 30°C. The cells were collected by centrifugation. The cells obtained from 10 ml. of the medium (activity of the enzyme: 20 u) were added to 10 ml. of 5 × 10⁻¹ M ammonium buffer solution (pH 9.5) containing 5 mmol. of β-chloro-L-alanine, 5 mmol. of sodium sulfide, 0.05% sodium dodecyl sulfate, an amount of pyridoxal phosphate to effect a concentration of 0.1 mM, and the required amount of the substance shown in Table 6 to achieve the listed concentrations. The reaction was carried out at 30°C for 3 hours. L-Cysteine was formed in the amounts shown in Table 6.

Table 6

| Added carbonyl compound | Concentration (M) | L-cysteine formed (mmol.) |
|---|---|---|
| Benzaldehyde | 0.2 | 2.64 |
| Isobutyraldehyde | 0.2 | 2.31 |
| Acetone | 0.7 | 4.01 |
| Methyl isobutyl ketone | 0.5 | 2.18 |
| Methyl ethyl ketone | 0.5 | 2.21 |
| Cyclohexanone | 0.5 | 2.05 |
| Benzophenone | 0.5 | 2.05 |
| Benzil | 0.2 | 2.12 |
| Pyruvic acid | 0.5 | 3.17 |
| 2-Oxobutyric acid | 0.5 | 3.01 |
| 2-Oxoglutaric acid | 0.5 | 2.02 |
| None | — | 1.82 |

EXAMPLE 7

To 10 ml. of 5 × 10⁻² M ammonium buffer solution (pH 9.5) containing 250 mg of β-chloro-L-alanine and a thiol shown in Table 2 was added 2.5 units of the purified enzyme obtained from *Enterobacter aerogenes* (*Aerobacter aerogenes*) (IFO 3320), and the reaction was carried out at 30°C for 1 hour. The cysteine derivatives shown in Table 7 were obtained.

Table 7

| Thiols | Amount added (mg) | Cysteine derivative | Amount formed (mg) |
|---|---|---|---|
| methanethiol | 100 | S-methyl-L-cysteine | 30 |
| ethanethiol | 130 | S-ethyl-L-cysteine | 42 |
| n-propanethiol | 160 | S-(n-propyl)-L-cysteine | 27 |

EXAMPLE 8

The cells obtained from 100 ml. of the medium in Example 4 (activity of the enzyme: about 60 u) were added to 10 ml. of 0.1 M ammonium buffer solution (pH 9.5) containing 2 mmol. of an amino acid shown in Table 8, 2 mmol. of a thiol shown in Table 8, 0.05% sodium dodecyl sulfate and pyridoxal phosphate in a concentration of 1 mM. The reaction was carried out at 30°C for 3 hours. The derivatives of L-cysteine shown in Table 8 were formed.

Table 7-continued

| Thiols | Amount added (mg) | Cysteine derivative | Amount formed (mg) |
|---|---|---|---|
| 2-propanethiol | 160 | S-allyl-L-cysteine | 3 |

Table 8

| Substrate Amino Acid | Thiol | Amino Acid Formed | Amount Formed (mmol.) |
|---|---|---|---|
| S-methyl-L-cysteine | n-propanethiol | S-(n-propyl)-L-cysteine | 0.08 |
| S-allyl-L-cysteine | methanethiol | S-methyl-L-cysteine | 0.03 |
| cysteine | methanethiol | S-methyl-L-cysteine | 0.04 |
| serine | methanethiol | S-methyl-L-cysteine | 0.01 |

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. A process for producing L-cysteine and derivatives thereof of the formula (I):

$$RS-CH_2CHCOOH \quad \quad (I)$$
$$\qquad \quad | $$
$$\qquad \; NH_2$$

wherein R is selected from the group consisting of hydrogen, $C_1 - C_{15}$ alkyl, $C_2 - C_{15}$ alkenyl, $C_6 - C_{15}$ aryl, $C_7 - C_{15}$ aralkyl, which comprises reacting β-substituted-L-alanine having the formula (II):

$$X-CH_2CHCOOH \quad \quad (II)$$
$$\qquad \quad | $$
$$\qquad \; NH_2$$

wherein X is selected from the group consisting of halogen, —OR' and —SR', erein R' is selected from the group consisting of hydrogen, allyl, $C_1 - C_{15}$ alkyl, $C_6 - C_{15}$ aryl and $C_7 - C_{15}$ aralkyl, with a thiol, or hydrogen sulfide, of the formula (III):

$$R - SH \quad \quad (III)$$

wherein R is as defined above, ammonium hydrosulfide or a metal hydrosulfide of the formula (IV):

$$R - S - Y \quad \quad (IV)$$

wherein R is hydrogen, and Y is ammonium or a metal, in an aqueous medium, in the presence of cysteine desulfhydrase.

2. The process of claim 1, wherein L-cysteine is produced by the reaction of β-substituted L-alanine of the formula (II) with a compound selected from the group consisting of hydrogen sulfide, ammonium hydrosulfide, a water-soluble metal hydrosulfide of the formula (IV), ammonium sulfide whereby ammonium hydrosulfide and/or hydrogen sulfide is produced in the aqueous medium, and a metal sulfide whereby said metal hydrosulfide and/or hydrogen sulfide is produced in the aqueous medium.

3. The process of claim 1, wherein the derivative of L-cysteine of the formula (I) is produced by the reaction of β-substituted L-alanine of the formula (II) with a thiol of the formula (III).

4. The process of claim 1, wherein R is selected from the group consisting of hydrogen, $C_1 - C_5$ alkyl and $C_2 - C_5$ alkenyl.

5. The process of claim 4, wherein R is selected from the group consisting of hydrogen, methyl, ethyl, n-propyl and allyl.

6. The process of claim 1, wherein R' is selected from the group consisting of hydrogen, allyl, and $C_1 - C_5$ alkyl.

7. The process of claim 6, wherein R' is selected from the group consisting of hydrogen, allyl and methyl.

8. The process of claim 1, wherein X is chlorine.

9. The process of claim 1, wherein ammonium sulfide which produces ammonium hydrosulfide and/or hydrogen sulfide in the aqueous medium or a water-soluble metal sulfide which produces a water-soluble metal hydrosulfide and/or hydrogen sulfide in the aqueous medium, is employed instead of hydrogen sulfide, ammonium hydrosulfide or a water-soluble metal hydrosulfide.

10. The process of claim 9, wherein said metal sulfide is selected from the group consisting of a sulfide of an alkali metal and an alkaline earth metal.

11. The process of claim 10, wherein said metal sulfide is selected from the group consisting of sodium sulfide, potassium sulfide, calcium sulfide and barium sulfide.

12. The process of claim 1, wherein said metal hydrosulfide is water-soluble.

13. The process of claim 12, wherein said metal hydrosulfide is selected from the group consisting of a hydrosulfide of an alkali metal and an alkaline earth metal.

14. The process of claim 13, wherein said metal hydrosulfide is selected from the group consisting of sodium hydrosulfide and potassium hydrosulfide.

15. The process of claim 1, wherein cysteine desulfhydrase is derived from a microorganism selected from the group consisting of Brevibacterium, Sarcina, Corynebacterium, Arthrobacter, Pseudomonas, Proteus, Micrococcus, Escherichia, Serratia, Alcaligenes, Bacillus, Agrobacterium, Enterobacter (Aerobacter), Citrobacter, Klebsiella and Salmonella.

16. The process of claim 1, wherein the reaction is carried out at a temperature of 30° – 50°C for a period of 2 – 48 hours in an aqueous medium having a pH of 7 – 11.

17. The process of claim 1, wherein 1 – 5 g/l of dried cells containing cysteine desulfhydrase is employed.

18. The process of claim 1, wherein the concentrations of β-substituted L-alanine, and the thiol, hydrogen sulfide, ammonium hydrosulfide or metal hydrosulfide are each 3 – 20 weight percent.

19. The process of claim 1, wherein said aqueous medium additionally contains a carbonyl compound containing 1 to 20 carbon atoms in a concentration of from 0.05 – 10 M.

20. The process of claim 19, wherein said carbonyl compound is selected from the group consisting of an α-keto carboxylic acid containing 3 to 20 carbon atoms, an aldehyde containing 1 to 20 carbon atoms, and a ketone containing 3 to 20 carbon atoms.

21. The process of claim 20, wherein said α-keto carboxylic acid, aldehyde or ketone is selected from the group consisting of benzaldehyde, isobutyraldehyde, acetone, methyl isobutyl ketone, methyl ethyl ketone, cyclohexanone, benzophenone, benzil, pyruvic acid, 2-oxobutyric acid and 2-oxoglutaric acid.

22. The process of claim 1, wherein said reaction is carried out in the presence of pyridoxal phosphate in a concentration of up to 0.01 mM.

* * * * *